United States Patent

Aulbach et al.

Patent Number: 5,767,300
Date of Patent: Jun. 16, 1998

[54] METALLOCENE COMPOUND

[75] Inventors: Michael Aulbach, Hofheim; Hans-Friedrich Herrmann, Dornheim; Dieter Bilda, Frankfurt; Carsten Bingel, Kriftel, all of Germany

[73] Assignee: Targor GmbH, Ludwigshafen, Germany

[21] Appl. No.: 681,636

[22] Filed: Jul. 29, 1996

[30] Foreign Application Priority Data

Jul. 28, 1995 [DE] Germany ............... 195 27 652.3

[51] Int. Cl.$^6$ ............... C07F 17/00; C07F 7/02; C07F 9/00

[52] U.S. Cl. ............... 556/7; 556/11; 556/12; 556/43; 556/53; 556/58; 556/82; 556/28; 502/103; 502/117; 502/158; 526/126; 526/160; 526/352; 526/943

[58] Field of Search ............... 556/11, 12, 7, 556/82, 43, 53, 58; 502/103, 117, 158; 526/126, 160, 352, 943

[56] References Cited

U.S. PATENT DOCUMENTS

| | | | |
|---|---|---|---|
| 3,010,982 | 11/1961 | Schaaf et al. | 260/439 |
| 4,769,510 | 9/1988 | Kaminsky et al. | 585/512 |
| 4,808,561 | 2/1989 | Welborn et al. | 502/104 |
| 4,874,734 | 10/1989 | Kioka et al. | 502/104 |
| 4,874,880 | 10/1989 | Miya et al. | 556/53 |
| 4,921,825 | 5/1990 | Kioka et al. | 502/104 |
| 4,985,576 | 1/1991 | Rohrmann et al. | 556/435 |
| 5,071,808 | 12/1991 | Antberg et al. | 502/107 |
| 5,126,301 | 6/1992 | Tsutsui et al. | 502/108 |
| 5,202,398 | 4/1993 | Antberg et al. | 526/129 |
| 5,324,800 | 6/1994 | Welborn et al. | 526/160 |
| 5,554,776 | 9/1996 | Langhauser et al. | 556/11 |

FOREIGN PATENT DOCUMENTS

| | | |
|---|---|---|
| 129 368 | 6/1984 | European Pat. Off. |
| 185 918 | 11/1985 | European Pat. Off. |
| 206 794 | 6/1986 | European Pat. Off. |
| 295 312 | 12/1987 | European Pat. Off. |
| 283 739 | 2/1988 | European Pat. Off. |
| 285 443 | 3/1988 | European Pat. Off. |
| 293 815 | 5/1988 | European Pat. Off. |
| 294 942 | 5/1988 | European Pat. Off. |
| 279 863 | 8/1988 | European Pat. Off. |

*Primary Examiner*—Porfirio Nazario-Gonzalez
*Attorney, Agent, or Firm*—Connolly & Hutz

[57] ABSTRACT

The present invention relates to a metallocene compound of the formula I which is suitable for olefin polymerization $$X_mM(L-M^2-A-ZR_o^3Hal_p)_n \atop {R^1 \atop | \atop R^2}} \quad (I)$$

where

M is a metal of group IVb, Vb or VIb of the Periodic Table.

X are each a hydrogen atom, a halogen atom or a $C_1-C_{40}$-radical $OR^4$ or $NR^4{}_2$, where $R^4$ are a $C_1-C_{20}$ hydrocarbon radical m and p are 1, 2 or 3.

n is 1 or 2.

L each a π ligand which coordinates to the central atom M.

$M^2$ are each a silicon atom, a germanium atom or a tin atom.

$R^1$ are a $C_1-C_{20}$-radical.

$R^2$ are a $C_1-C_{20}$-radical or a π ligand which coordinates to the central atom M.

A are each a bidentate $C_1-C_{40}$-hydrocarbon group.

Z are each a boron atom, a silicon atom, a germanium atom or a tin atom.

$R^3$ are each a hydrogen atom or a $C_1-C_{20}$-radical.

o is zero, 1 or 2.

Hal are each a halogen atom, and where n is 1 if $R^2$ is a π ligand which coordinates to the central atom M and n is 2 if $R^2$ is a $C_1-C_{20}$-radical.

15 Claims, No Drawings

METALLOCENE COMPOUND

DESCRIPTION

Metallocene Compound

The present invention relates to a metallocene compound which is suitable as a catalyst component for olefin polymerization. The invention also relates to a supported catalyst comprising the metallocene compound of the invention. In addition, the invention relates to a process for preparing a polyolefin using the metallocene compound of the invention.

Metallocene compounds, in particular those of the 4th transition group of the Periodic Table of the Elements, are suitable, in the presence of cocatalysts such as aluminoxanes, for polymerizing olefins (EP 129 368; EP-A 185 918; EP-A 283 739). The metallocene compounds contain π-ligands such as cyclopentadienyl groups which coordinate to the transition metal. They are very active in homogeneous catalysis, but give polymers having a poor polymer morphology. A further disadvantage when using homogeneous (i.e. soluble) metallocene-aluminoxane catalyst systems in processes in which the polymer formed is obtained as a solid is the formation of heavy deposits on reactor walls and stirrers. These deposits are formed by agglomeration of the polymer particles if the metallocene or the cocatalyst, or both, are present in dissolved form in the suspension medium. Such deposits in the reactors have to be removed regularly, since they rapidly reach considerable thicknesses, have a high strength and prevent heat exchange to the cooling medium.

To avoid reactor deposits and to improve the product morphology, metallocenes can be supported (EP 206 794; EP 294 942; EP 295 312; EP 279 863; EP 285 443). These supported catalyst systems have, however, a low activity and the metallocene components are frequently not sufficiently strongly anchored to the support and can thus be extracted by the hot suspension medium during the polymerization.

EP 293 815 describes unbridged metallocenes containing siloxane-substituted, halogen-free cyclopentadienyl ligands which are supported by reaction with a hydroxyl-containing support material. A disadvantage of this catalyst is that a high ratio of metallocene compound to support material is required, since the metallocene is only incompletely fixed to the support. A further disadvantage of these metallocenes is the limited range of syntheses, since the siloxane substituent is introduced into the cyclopentadienyl ring before complexation to the central atom.

JO 1259004 describes unbridged metallocenes which bear as substituents on the cyclopentadienyl ring $R_3Si$ groups bonded via an alkylene chain. These $R_3Si$ groups are able (as described in EP 293 815) to bond to hydroxyl-containing supports. Metallocenes having halogen-containing $R_3Si$ groups are not obtainable via the synthetic route described therein.

It is an object of the invention to provide a metallocene compound which avoids the disadvantages of the prior art and, in particular, ensures improved fixing to the support material and/or does not affect the polymerization properties.

It has now been found that these disadvantages can be avoided by a specific metallocene compound.

The present invention accordingly provides a metallocene compound of the formula I

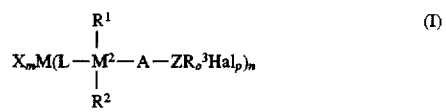

where

M is a metal of group IVb, Vb or VIb of the Periodic Table of the Elements.

X are identical or different and are each a hydrogen atom, a halogen atom or a $C_1$–$C_{40}$-radical such as $C_1$–$C_{10}$-alkyl, $C_1$–$C_{10}$-alkoxy, $C_6$–$C_{14}$-aryl, $C_6$–$C_{14}$-aryloxy, $C_2$–$C_{10}$-alkenyl, $C_7$–$C_{40}$-arylalkyl, $C_7$–$C_{40}$-alkylaryl, $C_8$–$C_{40}$-arylalkenyl, $OR^4$ or $NR^4{}_2$, where $R^4$ are identical or different and are each a $C_1$–$C_{20}$-hydrocarbon radical such as $C_1$–$C_{10}$-alkyl or $C_6$–$C_{14}$-aryl.

m is 1, 2 or 3.

n is 1 or 2.

L are identical or different and are each a π-ligand which coordinates to the central atom M.

$M^2$ are identical or different and are each a silicon atom, a germanium atom or a tin atom.

$R^1$ are identical or different and are each a $C_1$–$C_{20}$-radical.

$R^2$ are identical or different and are each a $C_1$–$C_{20}$-radical or a π-ligand which coordinates to the central atom M.

A are identical or different and are each a bidentate $C_1$–$C_{40}$-hydrocarbon group.

Z are identical or different and are each a boron atom, a silicon atom, a germanium atom or a tin atom.

$R^3$ are identical or different and are each a hydrogen atom or a $C_1$–$C_{20}$-radical.

o is zero, 1 or 2.

Hal are identical or different and are each a halogen atom, and p is 1, 2 or 3.

where n is 1 if $R^2$ is a n-ligand which coordinates to the central atom M and n is 2 if $R^2$ is a $C_1$–$C_{20}$-radical.

Preferred π-ligands are unsubstituted cyclopentadienyl groups or substituted cyclopentadienyl groups which preferably bear as radicals one or more $C_1$–$C_{30}$-hydrocarbon radicals, for example 2-methylcyclopentadienyl, methyl-tert-butylcyclopentadienyl, tert-butylcyclopentadienyl, isopropylcyclopentadienyl, dimethylcyclopentadienyl, trimethylcyclopentadienyl, 5-phenylcyclopentadienyl, diphenylcyclopentadienyl, indenyl, 2-methylindenyl, 2-ethylindenyl, 3-methylindenyl, 3-tert-butyl indenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthindenyl, 2-methyl-4,6-diisopropylindenyl, fluorenyl, 4-methylfluorenyl or 2,7-di-tert-butylfluorenyl. Particular preference is given to indenyl derivatives. The indenyl derivatives preferably bear a $C_1$–$C_{10}$-hydrocarbon radical such as $C_1$–$C_{10}$-alkyl on the five-membered ring, in particular in the 2 position, and on the six-membered ring are either unsubstituted or bear one or more $C_1$–$C_{20}$-hydrocarbon radicals such as $C_1$–$C_{10}$-alkyl, $C_6$–$C_{20}$-aryl (e.g. phenyl or naphthyl) or two or more of the $C_1$–$C_{20}$-hydrocarbon radicals form a ring system.

If $R^1$, $R^2$ and $R^3$ are $C_1$–$C_{40}$-radicals, these can be saturated or unsaturated, linear, cyclic or branched, for example a $C_1$–$C_{20}$-alkyl group, a $C_1$–$C_{20}$-haloalkyl group, a $C_6$–$C_{20}$-aryl group, a $C_6$–$C_{20}$-haloaryl group, a $C_2$–$C_{40}$-alkenyl group, a $C_7$–$C_{40}$-arylalkyl group, a $C_7$–$C_{40}$-alkylaryl group or a $C_8$–$C_{40}$-arylalkenyl group each of which can contain silicon, germanium, tin, oxygen, nitrogen, sulfur or phosphorus, e.g. a (tri($C_1$–$C_{10}$)-alkyl)silyl-$C_1$–$C_{20}$-alkyl group.

The bidentate $C_1$-$C_{40}$-hydrocarbon groups A can be saturated or unsaturated, linear, cyclic or branched, for example a $C_1$-$C_{20}$-alkylene group, a $C_6$-$C_{20}$-arylene group, a $C_2$-$C_{20}$-alkenylene group, a $C_7$-$C_{40}$-arylalkylene group, a $C_7$-$C_{40}$-alkylarylene group or a $C_8$-$C_{40}$-arylalkenylene group.

The metallocenes of the formula I can be unbridged (when n is 2) or bridged (when n is 1).

Preference is given to bridged metallocenes of the formula I in which

M is a metal of group IVb of the Periodic Table of the Elements, for example titanium, zirconium or hafnium, X are identical or different and are each a halogen atom or $C_1$-$C_{10}$ -alkyl, m is 2, n is 1, L is a substituted or unsubstituted cyclopentadienyl group which coordinates to the central atom M, $M^2$ is a silicon atom, $R^1$ is $C_1$-$C_{10}$-alkyl, $R^2$ is a substituted or unsubstituted cyclopentadienyl group which coordinates to the central atom M, A is a $C_1$-$C_{10}$-alkylene group, Z is a silicon atom, $R^3$ are identical or different and are $C_1$-$C_{10}$-alkyl or $C_6$-$C_{14}$-aryl, o is 0, 1 or 2, preferably 2, Hal are chlorine atoms, p is 1, 2 or 3, preferably 1.

Particular preference is given to bridged metallocenes of the formula I in which L and $R^2$ are identical.

Examples of the metallocenes of the invention are:

(4-trichlorosilyl-n-butyl)(methyl)silanediyl[bis(2-methylindenyl)]titanium dichloride
(4-trichlorosilyl-n-butyl)(methyl)silanediyl[bis(2-methylindenyl)]zirconium dichloride
(4-trichlorosilyl-n-butyl)(methyl)silanediyl[bis(2-methylindenyl)]hafnium dichloride
(4-trichlorosilyl-n-butyl)(methyl)silanediyl[bis(2-methylindenyl)]zirconium dichloride
(4-trichlorosilyl-n-butyl)(phenyl)silanediyl[bis(2-methylindenyl)]zirconium dichloride
(4-trichlorosilyl-n-butyl)(methyl)silanediyl[bis(2-methyl-4,5-benzoindenylindenyl)]zirconium dichloride
(4-trichlorosilyl-n-butyl)(methyl)silanediyl[bis(2-methyl-4-phenylindenyl)]zirconium dichloride
(4-trichlorosilyl-n-butyl)(methyl)silanediyl[bis(2-ethyl-4-phenylindenyl)]zirconium dichloride
(4-trichlorosilyl-n-butyl)(methyl)silanediyl[bis(2-methyl-4-naphthylindenyl)]zirconium dichloride
(3-trichlorosilyl-n-propyl)(methyl)silanediyl[bis(2-methylindenyl)]zirconium dichloride
(3-trichlorosilyl-n-propyl)(ethyl)silanediyl[bis(2-methylindenyl)]zirconium dichloride
(3-trichlorosilyl-n-propyl)(phenyl)silanediyl[bis(2-methylindenyl)]zirconium dichloride
(3-trichlorosilyl-n-propyl)(methyl)silanediyl[bis(2-methyl-4,5-benzoindenylindenyl)]zirconium dichloride
(3-trichlorosilyl-n-propyl)(methyl)silanediyl[bis(2-methyl-4-phenylindenyl)]zirconium dichloride
(3-trichlorosilyl-n-propyl)(methyl)silanediyl[bis(2-ethyl-4-phenylindenyl)]zirconium dichloride
(3-trichlorosilyl-n-propyl)(methyl)silanediyl[bis(2-methyl-4-naphthylindenyl)]zirconium dichloride
(3-trichlorosilyl-n-propyl)(methyl)silanediyl[(2-methylindenyl)(2-methyl-4,5-benzoindenylindenyl)]zirconium dichloride
(3-trichlorosilyl-n-propyl)(methyl)silanediyl[(2-methylindenyl)(2-methyl-4-phenylindenyl)]zirconium dichloride
(3-trichlorosilyl-n-propyl)(methyl)silanediyl[(2-methylindenyl)(2-ethyl-4-phenylindenyl)]zirconium dichloride
bis(4-trichlorosilyl-n-butyl)silanediyl[bis(4,5,6,7-tetrahydroindenyl)]zirconium dichloride
bis(4-trichlorosilyl-n-butyl)silanediyl[bis(2-methyl-4,6-diisopropylindenyl)]zirconium dichloride
bis(4-trichlorosilyl-n-butyl)silanediyl[bis(2-methylindenyl)]zirconium dichloride
bis(4-trichlorosilyl-n-butyl)silanediyl[bis(2-methyl-4,5 -benzoindenylindenyl)]zirconium dichloride
bis(4-trichlorosilyl-n-butyl)silanediyl[bis(2-methyl-4-phenylindenyl)]zirconium dichloride
bis(4-trichlorosilyl-n-butyl)silanediyl[bis(2-ethyl-4-phenylindenyl)]zirconium dichloride
bis(4-trichlorosilyl-n-butyl)silanediyl[bis(2-methyl-4-naphthylindenyl)]zirconium dichloride
bis(3-trichlorosilyl-n-propyl)silanediyl[bis(4,5,6,7-tetrahydroindenyl)]zirconium dichloride
bis(3-trichlorosilyl-n-propyl)silanediyl[bis(2-methyl-4,6-diisopropylindenyl)]zirconium dichloride
bis(3-trichlorosilyl-n-propyl)silanediyl[bis(2-methylindenyl)]zirconium dichloride
bis(3-trichlorosilyl-n-propyl)silanediyl[bis(2-methyl-4,5-benzoindenylindenyl)]zirconium dichloride
bis(3-trichlorosilyl-n-propyl)silanediyl[bis(2-methyl-4-phenylindenyl)]zirconium dichloride
bis(3-trichlorosilyl-n-propyl)silanediyl[bis(2-ethyl-4-phenylindenyl)]zirconium dichloride
bis(3-trichlorosilyl-n-propyl)silanediyl[bis(2-methyl-4naphthylindenyl)]zirconium dichloride
bis(8-trichlorosilyl-n-octyl)silanediyl[bis(4,5,6,7-tetrahydroindenyl)]zirconium dichloride
bis(8-trichlorosilyl-n-octyl)silanediyl[bis(2-methyl-4,6-diisopropylindenyl)]zirconium dichloride
bis(8-trichlorosilyl-n-octyl)silanediyl[bis(2-methylindenyl)]zirconium dichloride
bis(8-trichlorosilyl-n-octyl)silanediyl[bis(2-methyl-4,5-benzoindenylindenyl)]zirconium dichloride
bis(8-trichlorosilyl-n-octyl)silanediyl[bis(2-methyl-4-phenylindenyl)]zirconium dichloride
bis(8-trichlorosilyl-n-octyl)silanediyl[bis(2-ethyl-4-phenylindenyl)]zirconium dichloride
bis(8-trichlorosilyl-n-octyl)silanediyl[bis(2-methyl-4-naphthylindenyl)]zirconium dichloride
dimethylsilanediyl[(2-methylindenyl)(2-(4'-trichlorosilyl-n-butyl)indenyl)]zirconium dichloride
dimethylsilanediyl[(2-methylindenyl)(3-(4'-trichlorosilyl-n-butyl)indenyl)]zirconium dichloride
dimethylsilanediyl[(2-methylindenyl)(4-(4'-trichlorosilyl-n-butyl)indenyl)]zirconium dichloride
dimethylsilanediyl[(2-methylindenyl)(5-(4'-trichlorosilyl-n-butyl)indenyl)]zirconium dichloride
dimethylsilanediyl[(2-methylindenyl)(6-(4'-trichlorosilyl-n-butyl)indenyl)]zirconium dichloride
dimethylsilanediyl[(2-methylindenyl)(7-(4'-trichlorosilyl-n-butyl)indenyl)]zirconium dichloride
diphenylsilanediyl[(2-methylindenyl)(2-(4'-trichlorosilyl-n-butyl)indenyl)]zirconium dichloride
diphenylsilanediyl[(2-methylindenyl)(3-(4'-trichlorosilyl-n-butyl)indenyl)]zirconium dichloride
diphenylsilanediyl[(2-methylindenyl)(4-(4'-trichlorosilyl-n-butyl)indenyl)]zirconium dichloride
diphenylsilanediyl[(2-methylindenyl)(5-(4'-trichlorosilyl-n-butyl)indenyl)]zirconium dichloride diphenylsilanediyl[(2-methylindenyl)(6-(4'-trichlorosilyl-n-butyl)indenyl)]zirconium dichloride diphenylsilanediyl[(2-methylindenyl)(7-(4'-trichlorosilyl-n-butyl)indenyl)]zirconium dichloride dimethylsilanediyl[(2-methyl-4-phenylindenyl)(2-(4'-trichlorosilyl-n-butyl)indenyl)]zirconium dichloride dimethylsilanediyl[(2-methyl-4-phenylindenyl)(3-(4'-trichlorosilyl-n-butyl)indenyl)]zirconium dichloride dimethylsilanediyl[(2-methyl-4-phenylindenyl)(4-(4'-trichlorosilyl-n-butyl)indenyl)]zirconium dichloride dimethylsilanediyl[(2-methyl-4-phenylindenyl)(5-(4'-trichlorosilyl-n-butyl)indenyl)]zirconium dichloride dimethylsilanediyl[(2-methyl-4-phenylindenyl)(6-(4'-trichlorosilyl-n-butyl)indenyl)]zirconium dichloride dimethylsilanediyl[(2-methyl-4-phenylindenyl)(7-(4'-trichlorosilyl-n-butyl)indenyl)]zirconium dichloride

[cyclopentadienyl][(dimethylchlorosilyl-n-butyldimethylsilyl)cyclopentadienyl]zirconium dichloride

[cyclopentadienyl][(trichlorosilyl-n-butyldimethylsilyl)cyclopentadienyl]zirconium dichloride

[methylcyclopentadienyl][(dimethylchlorosilyl-n-butyldimethylsilyl)cyclopentadienyl]zirconium dichloride

[cyclopentadienyl][(dimethylchlorosilyl-n-octyidimethylsilyl)cyclopentadienyl]zirconium dichloride

[cyclopentadienyl][(dimethylchlorosilyl-n-butyldimethylsilyl)cyclopentadienyl]dimethylzirconium

[cyclopentadienyl][(dimethylchlorosilyl-n-butyldimethylsilyl)cyclopentadienyl]dibenzylzirconium

[cyclopentadienyl][(dimethylchlorosilyl-n-butyldimethylsilyl)cyclopentadienyl]diphenylzirconium

[indenyl][(dimethylchlorosilyl-n-butyldimethylsilyl)cyclopentadienyl]zirconium dichloride bis[(dimethylchlorosilyl-n-butyldimethylsilyl)cyclopentadienyl]zirconium dichloride bis[(trichlorosilyl-n-butyldimethylsilyl)cyclopentadienyl]zirconium dichloride bis[(dimethylchlorosilyl-n-butyldimethylsilyl)cyclopentadienyl]zirconium dichloride bis[(dimethylchlorosilyl-n-octyidimethylsilyl)cyclopentadienyl]zirconium dichloride bis[(dimethylchlorosilyl-n-butyldimethylsilyl)cyclopentadienyl]dimethyzirconium bis[(dimethylchlorosilyl-n-butyldimethylsilyl)cyclopentadienyl]dibenzylzirconium bis[(dimethylchlorosilyl-n-butyldimethylsilyl)cyclopentadienyl]diphenylzirconium bis[(dimethylchlorosilyl-n-butyldimethylsilyl)cyclopentadienyl]zirconium dichloride dimethylsilanediyl[bis(2-(4'-trichlorosilyl-n-butyl)indenyl]zirconium dichloride dimethylsilanediyl[bis(3-(4'-trichlorosilyl-n-butyl)indenyl)]zirconium dichloride dimethylsilanediyl[bis(4-(4'-trichlorosilyl-n-butyl)indenyl)]zirconium dichloride dimethylsilanediyl[bis(5-(4'-trichlorosilyl-n-butyl)indenyl)]zirconium dichloride dimethylsilanediyl[bis(6-(4'-trichlorosilyl-n-butyl)indenyl)]zirconium dichloride dimethylsilanediyl[bis(7-(4'-trichlorosilyl-n-butyl)indenyl)]zirconium dichloride dimethylsilanediyl[(2-methylindenyl)(2-(4'-trichlorosilyl-n-butylindenyl)]zirconium dichloride.

The metallocenes of the formula I can be prepared by addition of compounds of the formula $HZR^3_cHal_p$ onto metallocenes which bear as substituent a group containing a double bond. Metallocenes having unsaturated substituents and their preparation are known (Organometallics 1993, Volume 2, pages 2140–2151; C.R. Acad. Sci. Paris, Volume 284, pages 323–325; EP 372 414; EP 586 168; EP 647 650; DE 4 100 761). The reaction of metallocenes having a double bond as substituent with poly (methylhydrogensiloxane) is described in EP 372 414.

The present invention also provides a process for preparing a polyolefin by polymerization of at least one olefin in the presence of a catalyst comprising at least one metallocene compound of the formula I and at least one cocatalyst. The term polymerization includes both homopolymerization and copolymerization.

Preference is given to homopolymerizing or copolymerizing olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene. In the process of the invention, preference is given to homopolymerizing ethylene or propylene, or copolymerizing ethylene with one or more 1-olefins having from 3 to 20 carbon atoms, for example propylene, and/or one or more dienes having from 4 to 20 carbon atoms, for example 1,4-butadiene. Examples of such copolymers are ethylene-propylene copolymers and ethylene-propylene-1,4-hexadiene copolymers.

The polymerization is preferably carried out at a temperature of from −60° to 250° C., particularly preferably from 50° to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. A preferred embodiment is gas-phase polymerization.

The catalyst used in the process of the invention preferably comprises one metallocene compound of the formula 1. It is also possible to use mixtures of two or more metallocene compounds of the formula 1, or mixtures of metallocene compounds of the formula I with other metallocenes, semi-sandwich compounds or classical Ziegler-Natta catalysts, e.g. for preparing polyolefins having a broad or multimodal molecular weight distribution.

The metallocenes of the formula I are preferably used as racemates. However, it is also possible to use the pure enantiomer in the (+) or (−) form. The pure enantiomers enable an optically active polymer to be prepared. However, the meso form of the metallocenes should be separated off, since the polymerization-active center (the metal atom) in these compounds is no longer chiral owing to the mirror symmetry at the central metal atom and can therefore not produce a highly isotactic polymer. If the meso form is not separated off, atactic polymer is formed in addition to isotactic polymers. For certain applications, for example flexible moldings, this can be thoroughly desirable.

According to the invention, use is made of at least one cocatalyst which is preferably an aluminum compound and/or a boron compound. As aluminum compound, preference is given to an aluminoxane, particularly one of the formula IIa for the linear type and/or the formula IIb for the cyclic type

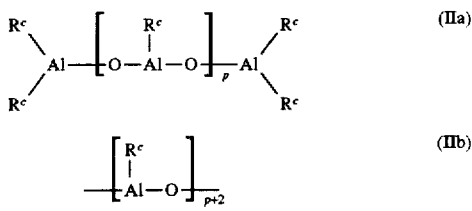

(IIa)

(IIb)

where, in the formulae IIa and IIb, the radicals $R^c$ can be identical or different and are each hydrogen or a $C_1$–$C_{20}$-hydrocarbon group such as a $C_1$–$C_6$-alkyl group, a $C_6$–$C_{18}$-aryl group or benzyl, and p is an integer from 2 to 50, preferably from 10 to 35.

The radicals $R^c$ are preferably identical and are methyl, ethyl, isobutyl, phenyl or benzyl, particularly preferably methyl.

If the radicals $R^c$ are different, they are preferably methyl and hydrogen or alternatively methyl and isobutyl, where hydrogen or isobutyl are preferably present in an amount of from 0.01 to 40% (number of the radicals $R^c$).

The aluminoxane can be prepared in various ways by known methods. One of the methods is, for example, reacting an aluminum-hydrocarbon compound and/or a hydridoaluminum-hydrocarbon compound with water (gaseous, solid, liquid or bound—for example as water of crystallization) in an inert solvent (for example toluene). To prepare an aluminoxane having different radicals $R^c$, for example, two different trialkylaluminums corresponding to the desired composition are reacted with water.

Regardless of the method of preparation, all aluminoxane solutions have in common a varying content of unreacted aluminum starting compound which is present in free form or as adduct.

It is possible to preactivate the (supported) metallocene with the cocatalyst, e.g. an aluminoxane, prior to use in the polymerization reaction. This significantly increases the polymerization activity and improves the particle morphology. The preactivation of the transition metal compound is carried out in suspension. Preferably, the (supported) metallocene is added to a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of $10^{-4}$-1 mol per mol of aluminoxane. The preactivation time is from 5 minutes to 60 hours, preferably from 5 to 60 minutes. It is carried out at a temperature of from $-78°$ to $100°$ C., preferably from $0°$ to $70°$ C.

According to the invention, it is also possible to use boron compounds, in particular those of the formulae $R^d{}_x NH_{4-x} BR^e{}_4$, $R^d{}_x PH_{4-x} BR^e{}_4$, $R^d{}_3 CBR^e{}_4$, $BR^e{}_3$, as cocatalysts. In these formula, x is a number from 1 to 4, preferably 3, the radicals $R^d$ are identical or different, preferably identical, and are $C_1$–$C_{10}$-alkyl, $C_6$–$C_{18}$-aryl or 2 radicals $R^d$ together with the atom connecting them to form a ring, and the radicals $R^e$ are identical or different, preferably identical, and are $C_6$–$C_{18}$-aryl which may be substituted by alkyl, haloalkyl or fluorine. In particular, $R^d$ is ethyl, propyl, butyl or phenyl and $R^e$ is phenyl, pentafluorophenyl, 3,5-bistrifluoromethylphenyl, mesityl, xylyl or tolyl (cf. EP 277 003, EP 277 004 and EP 426 638).

When using the abovementioned cocatalysts, the actual (active) polymerization catalyst is the reaction product of metallocene and one of the specified compounds. For this reason, this reaction product is preferably first prepared outside the polymerization reactor in a separate step using a suitable solvent.

According to the invention, a suitable cocatalyst is in principle any compound which, owing to its Lewis acidity, can convert the neutral metallocene into a cation and stabilize the latter ("labile coordination"). In addition, the cocatalyst or the anion formed therefrom should undergo no further reactions with the metallocene cation formed (cf. EP 427 697).

A prepolymerization can be carried out with the aid of the metallocene. The prepolymerization is preferably carried out using the (or one of the) olefin(s) used in the polymerization.

The catalyst used in the process of the invention is preferably supported. The application to a support allows, for example, the particle morphology of the polyolefin prepared to be controlled. The metallocene compound can here be reacted first with the support and subsequently with the cocatalyst. The cocatalyst can also be supported first and subsequently reacted with the metallocene compound. It is also possible to support the reaction product of metallocene compound and cocatalyst. Suitable support materials are, for example, silica gels, aluminum oxides, solid aluminoxane or other inorganic and organic support materials such as magnesium chloride. Another suitable support material is a polyolefin powder in finely divided form.

Suitable support materials are inorganic oxides, carbonates such as chalk, silicates such as talc and polymers having hydroxyl groups on the surface. Particularly suitable supports are porous oxides or mixed oxides of silicon and/or aluminum which have a specific surface area of from 50 to 1000 m$^2$/g, preferably from 100 to 800 m$^2$/g, in particular from 150 to 650 m$^2$/g, and whose pore volume is in the range from 0.2 to 3 cm$^3$/g, preferably from 0.4 to 3 cm$^3$/g, in particular from 0.6 to 2.7 CM$^3$/g. The particle size is from 1 to 500 µm, preferably from 10 to 200 µm, in particular from 20 to 100 µm. The number of hydroxyl groups is, depending on the specific surface area and the temperature pretreatment, in the range from 0.5 to 50 mmol, preferably from 1 to 20 mmol, in particular from 1.5 to 10 mmol, of hydroxyl groups per gram of support. Such oxides are sometimes prepared specifically with a view to use as supports for supported catalysts and are commercially available. Suitable support materials also include organic compounds and polymers bearing hydroxyl groups, for example polysaccharides, polyvinyl alcohol and cyclodextrin.

Before the support is reacted with the metallocene compound, adsorbed water has to be removed by drying at a temperature of from $120°$ to $800°$ C., preferably from $200°$ to $500°$ C., which can take from 1 to 10 hours. Drying is monitored analytically by titration of the OH content of the support material using n-butylmagnesium chloride. After drying, the support is stored with exclusion of air and water under an inert gas, for example nitrogen or argon.

The reaction of the support with the metallocene compound can be carried out by suspending the support in the inert solvent and allowing the dissolved metal locene compound to act on it at a temperature of from $0°$ to $80°$ C., preferably from $15°$ to $55°$ C., for from 1 to 1260 minutes, preferably from 20 to 180 minutes. The ratio of metal locene compound to support is selected as a function of the hydroxyl content in such a way that from 0.01 to 400 mmol, preferably from 0.02 to 10 mmol, of metallocene compound is used per gram of support. To neutralize the acid formed, from 0.01 to 400 mmol/g of a base, preferably from 20 to 25 mmol of dimethylaniline, is added.

Suitable solvents for the application to a support are solvents such as aliphatic or cycloaliphatic hydrocarbons, for example pentane, hexane, heptane, cyclohexane, methylcyclohexane, aromatic hydrocarbons such as benzene, toluene, xylene, petroleum or hydrogenated diesel oil fractions or ethers such as diethyl ether and THF which have carefully been freed of oxygen, sulfur compounds and moisture. Preference is given to using aliphatic and cycloaliphatic hydrocarbons.

After the reaction time has elapsed, the supernatant solution is separated off, for example by filtration or decantation. The remaining solid is washed from 1 to 5 times with an inert suspension medium such as toluene, n-decane, hexane, diesel oil or dichloromethane for removing soluble constituents in the catalyst formed, in particular for removing unreacted and therefore soluble metallocene.

The supported catalyst system thus prepared can be metered into the polymerization system as vacuum-dried powder or be resuspended while still containing solvent and metered as a suspension in one of the abovementioned inert suspension media into the polymerization system.

To remove catalyst poisons present in the olefin, purification using an aluminum alkyl, for example trimethylaluminum, triethylaluminum or triisobutylaluminum, is advantageous. This purification can be carried out either in the polymerization system itself, or the olefin is, prior to addition to the polymerization system, brought into contact with the Al compound and subsequently separated off again.

As molecular weight regulator and/or for increasing the activity, hydrogen is added if required. The total pressure in the polymerization system is from 0.5 to 100 bar. Preference is given to polymerization in the pressure range from 5 to 64 bar which is of particular interest in industry.

The metallocene is here used in a concentration, based on the transition metal, of from $10^{-3}$ to $10^{-8}$ mol, preferably from $10^{-4}$ to $10^{-7}$ mol, of transition metal per dm$^3$ of solvent or per dm$^3$ of reactor volume. The aluminoxane is used in a concentration of from $10^{-5}$ to $10^{-1}$ mol, preferably from $10^{-4}$ to $10^{-2}$ mol, per dm$^3$ of solvent or per dm$^3$ of reactor volume. The other cocatalysts mentioned are used in approximately equimolar amounts to the metallocene. However, higher concentrations are also possible in principle.

If the polymerization is carried out as a suspension or solution polymerization, use is made of an inert solvent customary for the Ziegler low-pressure process. For example, it is carried out in an aliphatic or cycloaliphatic hydrocarbon, examples being propane, butane, hexane, heptane, isooctane, cyclohexane, methylcyclohexane. It is also possible to use a petroleum or hydrogenated diesel oil fraction. Toluene can also be used. Preference is given to carrying out the polymerization in the liquid monomer.

If inert solvents are used, the monomers are metered in in gaseous or liquid form.

The polymerization time can be any desired, since the catalyst system to be used according to the invention displays only a small time-dependent drop in the polymerization activity.

Before addition of the catalyst, in particular the supported catalyst system, another aluminum alkyl compound such as trimethylaluminum, triethylaluminum, triisobutylaluminum, trioctylaluminum or isoprenylaluminum can be additionally added to the reactor to make the polymerization system inert (for example for removing catalyst poisons present in the olefin, i.e. as scavenger). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables the molar Al/M$^1$ ratio to be made small in the synthesis of a supported catalyst system.

The metallocenes of the invention are particularly suitable as catalyst components for preparing polyolefins.

The metallocenes of the invention also have an improved support behavior and are suitable for avoiding reactor deposits.

The following examples illustrate the invention:

EXAMPLE 1

Preparation of (4-trichlorosilyl-n-butyl)(methyl) silanediyl[bis(2-methylindenyl)]zirconium dichloride 0.4 g (3 mmol) of trichlorosilane and 10 mg of H$_2$PtCl$_6$.6H$_2$O were added to a solution of 0.52 g (1 mmol) of (3-butenyl)(methyl)silanediyl[bis(2-methylindenyl)] zirconium dichloride in 5 ml of toluene. After stirring for 24 hours at room temperature, the excess trichlorosilane and the toluene were removed in an oil pump vacuum. This gives 0.69 g of an oil which no longer shows any resonance signals of the vinyl protons in the $^1$H-NMR spectrum.

EXAMPLE 2

Preparation of dimethylsilanediyl[(2-methylindenyl) (2-(4'-trichlorosilyl-n-butyl)indenyl)]zirconium dichloride Using a method similar to Example 1, 0.52 g (1 mmol) of dimethylsilanediyl[(2-methylindenyl)(2-(3'-butenyl) indenyl)]zirconium dichloride was reacted with 0.25 g (1.8 mmol) of trichlorosilane and 7 mg of H$_2$PtCl$_6$.6H$_2$O. This gives 0.66 g of an oil which no longer shows any resonance signals of the vinyl protons in the $^1$H-NMR spectrum.

EXAMPLE 3

Preparation of cyclopentadienyl[ (dimethylchlorosilyl-n-butyldimethylsilyl) cyclopentadienyl]zirconium dichloride Using a method similar to Example 1, 0.8 g (2 mmol) of cyclopentadienyl[3'-butenyldimethylsilyl)cyclopentadienyl] zirconium dichloride was reacted with 0.4 g (4 mmol) of dimethylchlorosilane and 10 mg of H$_2$PtCl$_6$.6H$_2$O. This gives 1.1 g of an oil which no longer shows any resonance signals of the vinyl protons in the $^1$H-NMR spectrum.

EXAMPLE 4

Using a method similar to Example 1, 0.6 g (1.2 mmol) of bis[cyclopentadienyl(2'-propenyldimethylsilyl)] zirconium dichloride was reacted with 0.5 g (3.7 mmol) of trichlorosilane and 4 mg of H$_2$PtCl$_6$.6H$_2$O. After stirring for 24 hours at room temperature, the excess silane and the toluene were removed under reduced pressure giving 0.9 g of an oil whose $^1$H-NMR showed that the vinyl groups of the starting compound had been hydrosilylated to an extent of about 75%.

EXAMPLE 5

3 g of silicon dioxide (1.86 mmol of OH groups/g) were suspended in 30 ml of toluene and 1.1 mmol of dimethylaniline. At 0° C., 836 mg (1.1 mmol) of [Cl$_3$Si(CH$_2$)$_3$ Me$_2$SiCp)]$_2$ZrCl$_2$ dissolved in 30 ml of toluene are added. The mixture is stirred for a further 10 hours at 50° C. The solid is filtered off, washed twice with 15 ml each time of diethyl ether, twice with 20 ml each time of toluene and dried under reduced pressure. Zr content: 0.3 mmol/g.

EXAMPLE 6

In succession, a suspension of 100 mg (0.03 mmol of Zr) of the catalyst component from Example 4 in 4 ml of a methylaluminoxane solution in toluene (6 mmol of aluminum) and 700 ml of butane were placed in a 1 l polymerization autoclave. 4 bar of ethylene were subsequently passed in to a final pressure of 4 bar and polymerization was carried out for 1 hour. This gives 65.3 g of polyethylene having a bulk density of 333 g/l.

What is claimed is:

1. A metallocene compound of the formula I

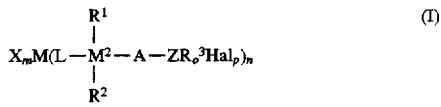

where

M is a metal of group IVb, Vb or VIb of the Periodic Table of the Elements, and is a central atom, X are identical or different and are each a hydrogen atom, a halogen atom or a $C_1$–$C_{40}$-radical, m is 1, 2 or 3, n is 1 or 2, L are identical or different and are each a π ligand which coordinates to the central atom M, $M^2$ are identical or different and are each a silicon atom, a germanium atom or a tin atom, $R^1$ are identical or different and are each a $C_1$–$C_{20}$-radical, $R^2$ are identical or different and are each a $C_1$–$C_{20}$-radical or a π-ligand which coordinates to the central atom M, A are identical or different and are each a bidentate $C_1$–$C_{40}$-hydrocarbon group, Z are identical or different and are each a boron atom, a silicon atom, a germanium atom or a tin atom, $R^3$ are identical or different and are each a hydrogen atom or a $C_1$–$C_{20}$-radical, o is zero, 1 or 2, Hal are identical or different and are each a halogen atom, and p is 1, 2 or 3, where n is 1 if $R^2$ is a π-ligand which coordinates to the central atom M and n is 2 if $R^2$ is a $C_1$–$C_{20}$-radical.

2. A catalyst component comprising the combination of components comprising at least one metallocene compound of the formula I as claimed in claim 1 combined with at least one cocatalyst.

3. A supported catalyst comprising a catalyst component as claimed in claim 2 and a support.

4. A process for preparing an olefin polymer by polymerization of one or more olefins which comprises polymerizing said one or more olefins in the presence of a metallocene compound of the formula I as claimed in claim 1.

5. A catalyst component as claimed in claim 2, wherein said cocatalyst is an aluminoxane.

6. A metallocene compound of formula I as claimed in claim 1, wherein:

M is a metal of Group IVb of the Periodic Table; the X groups are identical or different and are halogens or $C_1$–$C_{10}$ alkyl groups, m is 2, n is 1, L is a substituted or unsubstituted cyclopentadienyl group which coordinates to the central atom M, $M^2$ is a silicon atom, $R^1$ is $C_1$–$C_{10}$ alkyl, $R^2$ is a substituted or unsubstituted cyclopentadienyl group which coordinates to the central atom M, A is a $C_1$–$C_{10}$ alkylene group, Z is a silicon atom, and the $R^3$ groups are identical or different and are $C_1$–$C_{10}$ alkyl or $C_6$–$C_{14}$-aryl.

7. A metallocene compound of formula I as claimed in claim 6, wherein said substituted cyclopentadienyl group is an indenyl or substituted indenyl group.

8. A metallocene compound of formula I of claim 1, wherein n is 2, and $R^1$ and $R^2$ are same or different and are $C_1$–$C_{10}$ alkyl.

9. A metallocene compound of formula I as claimed in claim 8, wherein L of said formula I is a substituted or unsubstituted cyclopentadienyl group; M is a metal of Group IVb of the Periodic Table of the Elements; and Z is silicon.

10. A metallocene compound of formula I as claimed in claim 9, wherein said compound is a dialkylsilanediyl(2-methylindenyl)(trichloro-silylalkyl-substituted indenyl) zirconiumdihalide.

11. A metallocene compound of formula I of claim 1, wherein n is 1, L of said formula I is a substituted or unsubstituted cyclopentadienyl group; M is a metal of Group IVb of the Periodic Table of the Elements; and Z is silicon.

12. A (trihalosilyl-substituted alkyl)(alkyl)silane diyl [bis (substituted or unsubstituted indenyl)] zirconium dihalide.

13. A catalyst component comprising the combination of components consisting essentially of at least one metallocene compound of the formula I as claimed in claim 1 combined with at least one cocatalyst.

14. A supported component comprising the catalyst component as claimed in claim 13 and a support cocatalyst.

15. A catalyst component as claimed in claim 14, wherein said cocatalyst is an aluminoxane.

* * * * *